United States Patent
Obst et al.

(10) Patent No.: US 10,660,786 B2
(45) Date of Patent: May 26, 2020

(54) CONTAINMENT DEVICES FOR TREATMENT OF INTESTINAL FISTULAS AND COMPLEX WOUNDS

(71) Applicant: Fistula Solution Corporation, Scandia, MN (US)

(72) Inventors: Andrew Thomas Obst, Scandia, MN (US); Maryanne Ruth Obst, Scandia, MN (US); David James Dries, Woodbury, MN (US)

(73) Assignee: Fistula Solution Corporation, Scandia, MN (US)

( * ) Notice: Subject to any disclaimer, the term of this patent is extended or adjusted under 35 U.S.C. 154(b) by 1134 days.

(21) Appl. No.: 14/931,204

(22) Filed: Nov. 3, 2015

(65) Prior Publication Data
US 2016/0120687 A1  May 5, 2016

Related U.S. Application Data

(60) Provisional application No. 62/122,965, filed on Nov. 3, 2014.

(51) Int. Cl.
*A61F 5/443* (2006.01)
*A61F 5/445* (2006.01)
*A61M 1/00* (2006.01)

(52) U.S. Cl.
CPC .............. *A61F 5/443* (2013.01); *A61F 5/445* (2013.01); *A61M 1/0088* (2013.01)

(58) Field of Classification Search
CPC combination set(s) only.
See application file for complete search history.

(56) References Cited

U.S. PATENT DOCUMENTS

| | | | |
|---|---|---|---|
| 3,398,744 A * | 8/1968 | Hooper | A61F 5/445 604/340 |
| 5,636,643 A | 6/1997 | Argenta et al. | |
| 6,099,508 A | 8/2000 | Bousquet | |

(Continued)

FOREIGN PATENT DOCUMENTS

WO   WO 2011/031822 A1   3/2011

OTHER PUBLICATIONS

Search Report and Written Opinion for PCT Application No. PCT/US2015/058740 dated Feb. 3, 2016, 16 pages.

(Continued)

*Primary Examiner* — Tatyana Zalukaeva
*Assistant Examiner* — Guy K Townsend
(74) *Attorney, Agent, or Firm* — Patterson Thuente Pedersen, P.A.

(57) ABSTRACT

Devices to contain and control the effluent or gastric juices of intestinal fistulas, other fistulas, stomas, and other wounds. The device includes a flexible fluid containment lineal strip defining a fluid containment wall which collapses when pressure is applied to the wound dressing, means for forming the lineal strip into any open or closed shape to fit wounds of various shape and size, means for joining the lineal strip to create closed effluent containment areas, means for creating a seal at the wound bed interface whereby effluent is contained, and means for interfacing with a pouch appliance to capture effluent and bowel contents until bowel contents can be emptied into a toilet or other waste receptacle.

20 Claims, 7 Drawing Sheets

(56) References Cited

U.S. PATENT DOCUMENTS

| | | | |
|---|---|---|---|
| 6,709,421 B1* | 3/2004 | Falconer | A61F 5/441 604/335 |
| 7,708,724 B2 | 5/2010 | Weston | |
| 8,409,157 B2 | 4/2013 | Haggstrom et al. | |
| 8,529,526 B2* | 9/2013 | Wilkes | A61F 13/00059 604/304 |
| 8,758,314 B2 | 6/2014 | Hall et al. | |
| 8,915,894 B1* | 12/2014 | Lonky | A61M 37/00 604/289 |
| 9,078,990 B1 | 7/2015 | Obst et al. | |
| 9,265,665 B2* | 2/2016 | Robinson | A61M 1/0031 |
| 10,182,947 B2* | 1/2019 | Hu | A61F 13/0213 |
| 2007/0191794 A1* | 8/2007 | Cline | A61F 5/445 604/335 |
| 2008/0161778 A1 | 7/2008 | Steward | |
| 2008/0287892 A1 | 11/2008 | Khan et al. | |
| 2009/0131893 A1 | 5/2009 | Priest et al. | |
| 2009/0192467 A1 | 7/2009 | Hansen et al. | |
| 2009/0209917 A1 | 8/2009 | Tanaka et al. | |
| 2010/0145293 A1 | 6/2010 | Verhaalen | |
| 2010/0262095 A1 | 10/2010 | Hall | |
| 2011/0040269 A1* | 2/2011 | Cline | A61F 5/445 604/335 |
| 2011/0137270 A1* | 6/2011 | Hu | A61F 13/0213 604/319 |
| 2012/0029450 A1* | 2/2012 | Grum-Schwensen | A61F 5/443 604/344 |
| 2014/0148771 A1* | 5/2014 | Luce | A61F 5/445 604/345 |
| 2014/0207027 A1* | 7/2014 | Navia | A61F 13/00068 601/6 |
| 2014/0309604 A1* | 10/2014 | Paratore | A61F 5/4407 604/332 |
| 2014/0324002 A1* | 10/2014 | Luce | A61F 5/448 604/338 |
| 2015/0100045 A1* | 4/2015 | Allen | A61M 27/00 604/543 |
| 2016/0120687 A1* | 5/2016 | Obst | A61F 5/445 604/337 |

OTHER PUBLICATIONS

Application and File history for U.S. Appl. No. 13/750,154, filed Jan. 25, 2013. Inventors: Obst et al.

Goverman et al., "The "Fistula VAC," a Technique for Management of Enterocutaneous Fistulae Arising within the Open Abdomen: Report of 5 Cases", The Journal of TRAUMA Injury, Infection, and Critical Care, vol. 60, No. 2, Feb. 2006, pp. 428-431.

Byrnes et al., "A Novel Technique to Skin Graft Abdominal Wall Wounds Surrounding Enterocutaneous Fistulas", Surgical Infections, vol. 11, No. 6, 2010, pp. 505-509.

Stremitzer et al., "Successful bridging treatment and healing of enteric fistulae by vacuum-assisted closure (VAC) therapy and targeted drainage in patients with open abdomen", International Journal of Colorectal Disease, vol. 26, 2011, pp. 661-666.

Aguila et al., "The Stool Shield: A Novel Approach to the Colo-Atmospheric Fistula", Journal of the American College of Surgeons, 2011, pp. e-17-e19.

Search Report dated May 2, 2018 for EP Application No. 15857923. 5, 9 pages.

* cited by examiner

CONTAINMENT DEVICES FOR TREATMENT OF INTESTINAL FISTULAS AND COMPLEX WOUNDS

RELATED APPLICATION

The present application claims the benefit of U.S. Provisional Application No. 62/122,965 filed Nov. 3, 2014, which is hereby incorporated herein in its entirety by reference.

BACKGROUND OF THE INVENTION

Complex abdominal wound care presents many challenges for healthcare professionals and patients. Particularly difficult to manage are enteric or intestinal fistulas which drain the contents of the bowel into open abdominal wounds. Fistulas are abnormal passages between organs that do not normally connect. In cases of intestinal fistulas, a passage from the intestines to the surface of the skin allows intestinal contents or effluent to spill onto a wound site and surrounding skin leading to infection, persistent tissue inflammation, and potentially sepsis. An intestinal fistula can produce seven liters or more of intestinal effluent per day that must be contained and controlled if the wound is to heal.

Intestinal fistulas often lie within a much larger abdominal wound bed. Abdominal wounds with fistulas can encompass large areas of the abdomen, measuring 20 centimeters or greater in diameter and 6 cm or more in depth. Malnutrition, frequent infectious complications, chronic pain, and depression are common in patients with this overwhelming condition. Operative management often requires lengthy procedures of six to ten hours with high risk of morbidity and mortality. To achieve good outcomes, operative repairs generally need to occur six to twelve months after initial identification of the intestinal fistula. Because of the lengthy interval between presentation of the intestinal fistula and definitive surgical repair, intervening wound management takes on a unique importance.

Negative Pressure Wound Therapy (NPWT) uses a vacuum source to compress wound filler dressings and is commonly applied to complex abdominal wounds to promote healing. NPWT holds promise in managing open wounds with intestinal fistulas; however the effectiveness of NPWT and other wound therapies have been limited by a persistent problem of wound filler dressing failure due to intestinal fistula effluent or gastric juice fouling. As a NPWT vacuum is applied to a wound bed that includes an intestinal fistula, the fistula's effluent is drawn into the NPWT wound filler dressing and across the entire wound bed. The effluent contamination causes tissue breakdown and infection, creates a loss of dressing vacuum seal as the system is overwhelmed with effluent, and necessitates frequent changes of expensive NPWT wound filler dressings.

A number of devices have been proposed to control the effluent and bowel contents from intestinal fistulas, including U.S. patent publications 2010/0145293 to Verhaalen, 2008/0161778 to Steward, and 2008/0287892 to Khan et al.; however none of the references appears to have been commercialized in a way that has practical application at the bedside and intestinal fistula wound dressing failure remains a common problem.

General disadvantages found with the references include: 1. Devices are not adaptable to comprehend the broad spectrum of intestinal fistula and other wound types. Different stages of fistula development and healing have different effluent control demands that are difficult to address with devices that are not tailored to the specific wound. 2. Multi-component devices and multi-step device assembly create complexity for caregivers and may require specialized training or the expertise of a wound specialist. 3. Devices with rigid surfaces are very difficult to seal to the wound bed and are potentially dangerous to the intestine and adjacent tissue. Abdominal wound beds are dynamic and pliable surfaces and in practice we find that fistula effluent quickly finds its way past rigid devices and the wound dressing is fouled. Also, rigid devices tend to be uncomfortable for the patient and can aggravate the wound being treated. 4. Devices with thick containment walls and rigid flanges cannot be placed over fistulas and wounds that are in close proximity to the sides of the wound bed or underneath the edges of the abdominal wall and can cause tissue, intestinal, or other structural damage. 5. Devices that rely on ostomy adhesive to create a seal between the device and the wound site have poor longevity. In practice we find that these adhesives do not adhere to wet, weeping wound beds and adhesion generally fails. As adhesion is lost, fistula effluent is drawn past the device and wound dressing is fouled.

An embodiment of the "isolation component" described in U.S. patent publication 2010/0145293 is demonstrated online at http://www.youtube.com/watch?v=fOGpffzZvSY for use on intestinal fistula patients. However, this device has specific disadvantages. 1. The device is too complex for bedside nurses or homecare nurses to assemble without the help of a wound specialist. 2. The device fails to stay in the desired location when compressed with NPWT. 3. The device does not maintain desired form when compressed with NPWT and effluent is drawn past the device and wound dressing is fouled. 4. Caregivers often give up on the technique after repeated failures.

The present disclosure provides devices improved over the prior patent references and prior products.

SUMMARY

Embodiments according to the disclosure are directed to devices to contain and control the effluent or gastric juices of intestinal fistulas, other fistulas, stomas, and other wounds, comprises a flexible fluid containment lineal strip, fluid containment walls which collapse when pressure is applied to the wound dressing, means for forming the lineal strip into any open or closed shape to fit wounds of various shape and size, means for joining the lineal strip to create closed effluent containment areas, means for creating a seal at the wound bed interface whereby effluent is contained, and means for interfacing with a pouch appliance to capture effluent and bowel contents until bowel contents can be emptied into a toilet or other receptacle for disposing of waste.

Accordingly, this disclosure describes numerous intestinal fistula devices having various aspects and advantages. The disclosure provides devices, which are simple in construction, to contain and control the effluent and bowel content from intestinal fistulas, other fistulas, stomas, and other wounds so dressings can be applied and changed by nonspecialized bedside or homecare nurses. These devices seal to the wound bed and do not allow effluent to be drawn past the seal, even with negative pressure wound therapy (NPWT) or other wound care techniques, that might be used to extend dressing life and/or establish effective conditions for wound healing. The devices hold themselves in the intended location, even with the application of NPWT and/or other wound therapies, during normal daily activity of the patient. The devices mitigate the need for ostomy adhesive, which reduces the frequency of wound dressing changes due to ostomy adhesive failure. The devices can be custom cut (e.g., at bedside) to best fit the device to irregular surfaces of wound beds or isolate a fistula or wound that is in close proximity to the sides of the wound bed or underneath the edges of the abdominal wall. The devices are flexible and collapse symmetrically when part of NPWT or other wound therapy to prevent deformation or buckling over and related aggravation of the fistula, intestine, or wound. The devices isolate the intestinal fistula or wound from suction or vacuum, thus protecting the bowel or wound site from negative pressures. The devices are adaptable to a broad spectrum of intestinal fistula, ostomy, and other wound types. Overall, the devices improve the healing process and thus improve the quality of patient life, by allowing patients to return to their normal life and work routines during the healing process.

These and various other features and advantages will be apparent from a reading of the following detailed description.

BRIEF DESCRIPTION OF THE DRAWING

The invention may be more completely understood in consideration of the following detailed description of various embodiments of the invention in connection with the accompanying drawing, in which.

DETAILED DESCRIPTION OF THE INVENTION

Figure 1A:
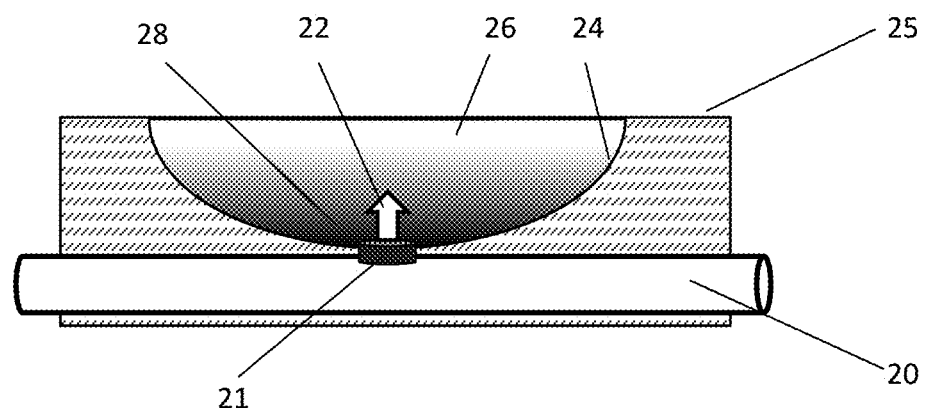
FIG. 1A is a cross-sectional view of an abdominal wound with an intestinal fistula or ostomy that has fouled the wound filler dressing.

Embodiments of the present disclosure provide various embodiments of intestinal fistula and ostomy healing devices, configured for application around a fistula, ostomy, or other wound to physically separate the fistula or ostomy from the remainder of the wound bed area, such that any effluent from the intestine or bowel, or other enteric substances, that pass through the fistula or ostomy are prevented from communicating with the wound bed area.

All of the devices have a flexible fluid containment lineal strip, fluid containment walls which collapse when pressure is applied to the wound dressing, means for forming the lineal strip into any open or closed shape to fit wounds of various shape and size, means for joining the lineal strip to create shaped containment areas, means for creating a seal at the wound bed interface whereby effluent is contained, and means for interfacing with a pouch appliance to capture effluent and bowel contents until bowel contents can be emptied into a toilet.

The device is collapsible, from a first height to a second height less than the first height. When the device is in a relaxed state (e.g., not installed on a wound), the device has its first height, and when the device is in its collapsed or "use" state (e.g., installed on a wound), the device has its second height. In some embodiments, the first height is at least ½ inch and no more than 5 inches, and more particularly from 1 inch to 2 inches The second height is less than the first height, in some embodiments no more than 1 inch, in other embodiment no more than ½ inch, and in other embodiments no more than ¼ inch. The rigidity and thus collapsibility of the device can be adjusting by modifying the material and thickness of the fluid containment wall, and by including features such as ribs or bellows in the fluid containment wall.

As used herein, "collapse", "collapsible" and variations thereof means that the structure, particularly the side wall structure of the fluid containment lineal strip, folds, falls in, crumbles, or otherwise decreases upon itself. In some embodiments of "collapse", the wall may fold upon itself to form a region that has a doubled wall; however, embodiments where two discrete (unconnected) pieces are slid or otherwise moved in overlapping relation to each other is not considered to be a collapse of the pieces. In some embodiments of "collapse", the wall may compress along the longitudinal axis of the fluid containment wall, thus forming folds, creases and the like in the wall.

In use, the device is placed in a wound bed such that the fluid containment wall surrounds a fistula, ostomy or other wound opening. By being so positioned, the device separates and isolates the fistula from the remainder of the wound bed area. This separation prevents or reduces any intestinal effluent or other enteric substance passing out of the fistula from coming into contact with the wound bed area surrounding the fistula, as the effluent will be at least initially retained within the interior volume of the fluid containment wall. This promotes healing of the wound bed and lowers the chances for infection.

In the following description, reference is made to the accompanying drawings that form a part hereof and in which are shown by way of illustration several specific embodiments. The following reference numbers are used throughout the drawings:

20 intestine
21 intestinal fistula or ostomy
22 intestinal content or effluent
24 wound bed
25 abdominal tissue
26 wound filler dressing (e.g. open cell foam)
28 wound filler dressing (e.g. open cell foam) contaminated with intestinal content or effluent
30 flexible fluid containment lineal strip device
32 end joint for flexible fluid containment lineal strip device
34 end joint seal for flexible fluid containment lineal strip device
36 effluent containment area
40 collapsible fluid containment wall
42 pleats in the fluid containment wall
44 configurable (e.g. can be cut to fit), flexible flange on device top surface; appliance interface; seating area for pouch appliances that capture intestinal fistula, stoma and wound effluent or bowel contents
46 configurable (e.g. can be cut to fit), flexible flange on device base
48 configurable (e.g. can be cut to fit), flexible skirt along device base
49 open cell foam or other wound dressing material
50 flat fluid containment wall
51 curved fluid containment wall -continued 52 ribbing in the fluid containment wall
53 bellows in the fluid containment wall
54 device without skirt along device base
55 plurality of configurable (e.g. can be cut to fit), flexible skirts along device base
56 configurable (e.g. can be cut to fit), flexible flange along interior fluid containment wall base
57 moldable, formable component (e.g. wire or bar)
60 device without open cell foam or other wound dressing material
61 device with rounded open cell foam or other wound dressing material
62 device with angular open cell foam or other wound dressing material
63 unitary embodiment of flexible fluid containment lineal strip device
64 impermeable surface to liquid and air
65 permeable surface to liquid and air
66 barb(s), ridge(s), or bump(s) to retain open cell foam or other wound dressing material
67 flexible bulb seal, solid or hollow, along device base
68 adhesive backing to retain open cell foam or other wound dressing material
70 cuts or cut lines in flange on device top surface
72 cuts or cut lines in flange on device base
80 pleats or folds in flange on device top surface
82 pleats or folds in flange on device base
90 stretchable or moldable sections in flange on device top surface
92 stretchable or moldable sections in flange on device base The following description provides additional specific embodiments. It is to be understood that other embodiments are contemplated and may be made without departing from the scope or spirit of the present disclosure. The following detailed description, therefore, is not to be taken in a limiting sense. While the present disclosure is not so limited, an appreciation of various aspects of the disclosure will be gained through a discussion of the examples provided below.

Unless otherwise indicated, all numbers expressing feature sizes, amounts, and physical properties are to be understood as being modified by the term "about." Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

FIG. 1A shows a cross-sectional view of an abdominal wound with an intestinal fistula or ostomy 21 that has fouled a wound filler dressing 26. The intestinal fistula or ostomy 21 communicates intestinal content or effluent 22 from an intestine 20 onto an open wound bed 24 that is surrounded by intact abdominal tissue 25. Common treatment includes the placement of wound filler dressing (e.g. open cell foam) 26 in a wound bed 24 to promote healing. However, intestinal content or effluent 22 contaminates the wound filler dressing 26 causing dressing failure due to intestinal fistula effluent fouling.

Figure 1B:
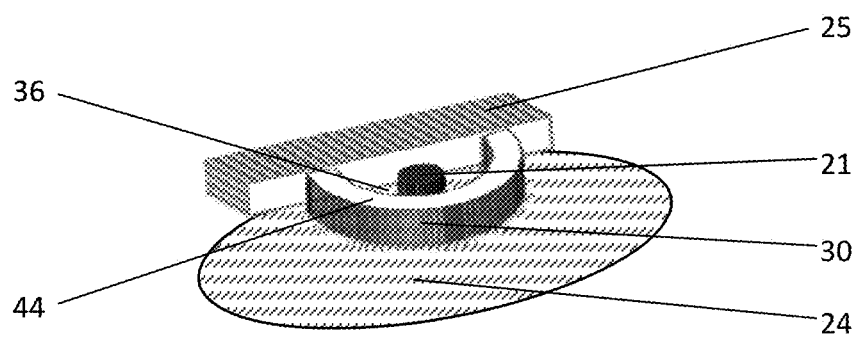
FIG. 1B is a perspective view of the employment of a device according to this disclosure, formed in an open shape to isolate an intestinal fistula or ostomy at the edge of a wound bed.

In an embodiment, FIG. 1B shows a first employment of a containment device 30 for treatment of intestinal fistulas and complex wounds. The flexible fluid containment lineal strip device 30 is formed in an open shape to isolate an intestinal fistula or ostomy 21 which is positioned at the edge of a wound bed 24 and is adjacent to intact abdominal tissue 25. The flexible fluid containment lineal strip device 30 is cut to length and formed to create a closed effluent containment area 36 between the device 30 and intact abdominal tissue 25. After the intestinal fistula or ostomy 21 is isolated, wound filler dressing (e.g. open cell foam) is placed in the surrounding wound bed 24. The surrounding wound filler dressing and flexible fluid containment lineal strip device 30 are together fixed in place with a covering adhesive wound drape membrane or other mechanism, and negative pressure or vacuum is typically initiated to compress the device 30 and wound filler dressing. Typically, an effluent collection pouch appliance is then adhesively bonded to appliance interface surface 44 to capture effluent and bowel contents from the intestinal fistula or ostomy 21. The pouch appliance can then be emptied into a toilet as needed.

Figure 1C:
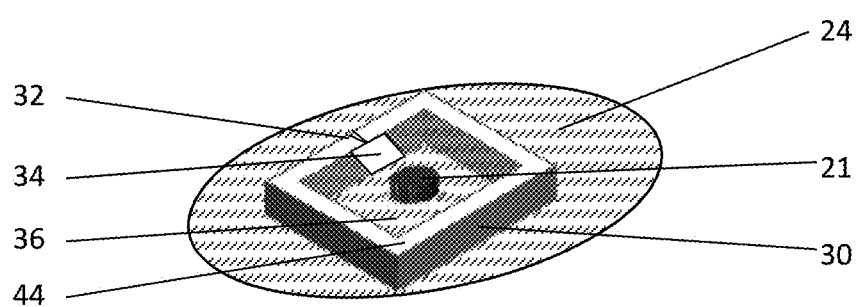
FIG. 1C is a perspective view of an alternative employment of a device according to this disclosure, formed and joined in a closed shape to isolate an intestinal fistula or ostomy near the center of a wound bed.

FIG. 1C shows a second employment of a containment device 30 for treatment of intestinal fistulas and complex wounds. The flexible fluid containment lineal strip device 30 is formed in a closed shape with overlapping or abutting joined end 32 to isolate an intestinal fistula or ostomy 21 near the center of a wound bed 24. The flexible fluid containment lineal strip device 30 is cut to length and formed to create a closed effluent containment area 36. The end joint 32 of the device 30 is joined with adhesive, tape, staples, sutures (e.g. bioabsorbable), interlocking or overlapping end profiles, or other means and the end joint seal 34 can be made with adhesive, tape, or other impermeable means. After the intestinal fistula or ostomy 21 is isolated, wound filler dressing (e.g. open cell foam) is placed in the surrounding wound bed 24. The surrounding wound filler dressing and flexible fluid containment lineal strip device 30 are together fixed in place with an adhesive wound drape membrane or other mechanism, and negative pressure or vacuum is typically initiated to compress the device 30 and wound filler dressing. Typically, an effluent collection pouch appliance is then adhesively bonded to appliance interface surface 44 to capture effluent and bowel contents from the intestinal fistula or ostomy 21. The pouch appliance can then be emptied into a toilet as needed.

Figure 2C:
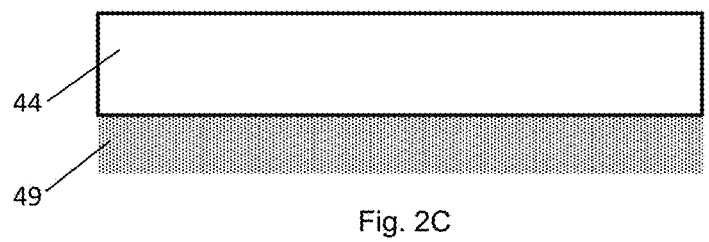
FIG. 2C is a top view of the device of FIG. 2A.
Figure 2B:
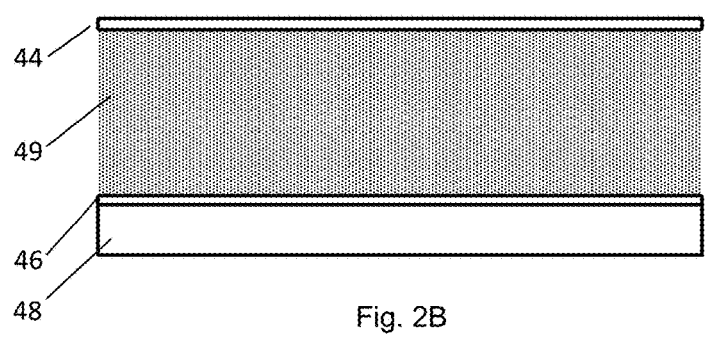
FIG. 2B is an outside view of the device of FIG. 2A.
Figure 2A:
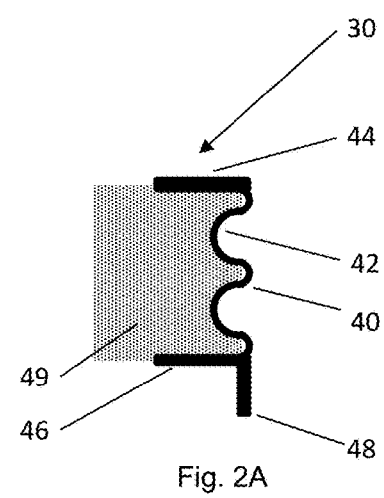
FIG. 2A is a cross-sectional view of an embodiment of a device according to this disclosure.
Figure 2D:
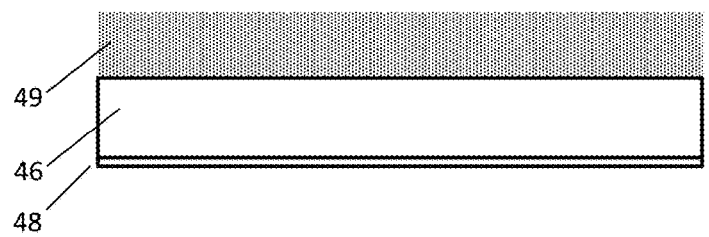
FIG. 2D is a bottom view of the device of FIG. 2A.

FIG. 2A shows a first embodiment of a containment device 30 for treatment of intestinal fistulas and complex wounds in cross section. FIG. 2B is an outer elevation view of the device 30 and wound dressing material 49 of FIG. 2A, FIG. 2C is a top view of the device 30 of FIG. 2A, and FIG. 2D is a bottom view of the device 30 of FIG. 2A. The flexible fluid containment lineal strip device 30 has a collapsible fluid containment sidewall 40 with pleats 42 to facilitate uniform collapse of the device 30 when compressed. A configurable (e.g. can be cut to fit), flexible flange 44 on device top surface functions as an appliance interface for seating pouch appliances that capture fistula, stoma and wound effluent. A configurable (e.g. can be cut to fit), flexible flange on the device base 46 is designed to seat the device 30 in the wound bed 24 and create a positive seal at the wound bed interface whereby effluent is contained. The surface of flange 46 may be textured to help seat device 30 in wound bed 24 and mitigate need for separate wound adhesives. Flange 46 can be custom cut (e.g., at bedside) to adapt device 30 to fit irregular wound beds. A configurable (e.g. can be cut to fit), flexible skirt 48 along the device base 46 is a secondary means for creating a seal at the wound bed interface to contain effluent. Skirt 48 may be custom cut for each patient (e.g., at bedside) to adapt device 30 to best fit irregular fistula or wound walls and mechanically block effluent from being drawn past device 30 and contaminating the surrounding wound dressing. Skirt 48 further creates a positive seal with the wound bed to contain effluent and direct it away from the fistula or wound and other nearby tissue to promote healing. And further, skirt 48 isolates the fistula or wound from negative pressure or vacuum. A strip of open cell foam or other wound dressing material 49 is attached to the outside of the device 30 and interfaces with surrounding wound filler dressing.

Figure 3A:
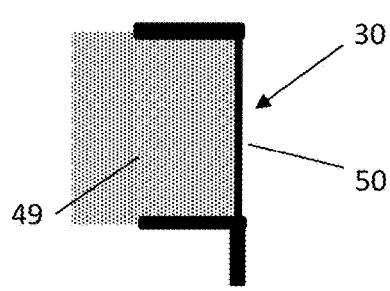
FIG. 3A is a cross-sectional view of an alternative embodiment of the device of FIG. 2A with a flat fluid containment wall.
Figure 3B:
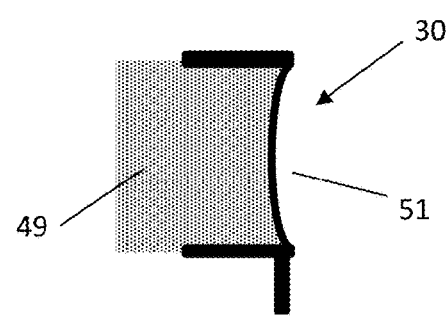
FIG. 3B is a cross-sectional view of an alternative embodiment of the device of FIG. 2A with a curved fluid containment wall.
Figure 3C:
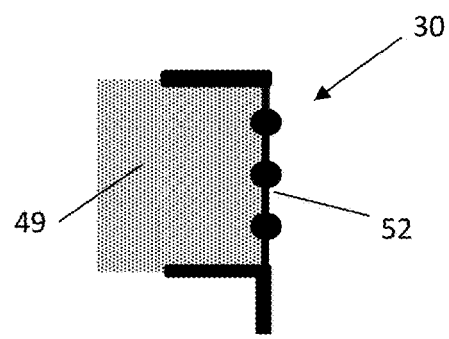
FIG. 3C is a cross-sectional view of an alternative embodiment of the device of FIG. 2A with ribbing in the fluid containment wall.
Figure 3D:
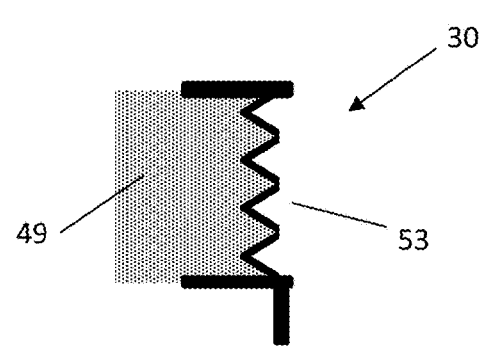
FIG. 3D is a cross-sectional view of an alternative embodiment of the device of FIG. 2A with bellows in the fluid containment wall.
Figure 3E:
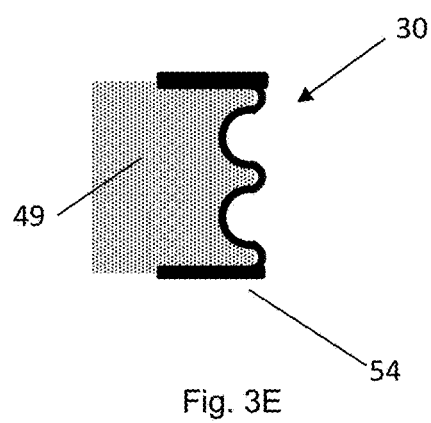
FIG. 3E is a cross-sectional view of an alternative embodiment of the device of FIG. 2A without a skirt along device base.
Figure 3F:
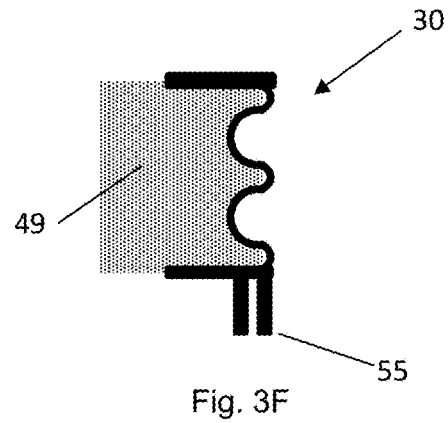
FIG. 3F is a cross-sectional view of an alternative embodiment of the device of FIG. 2A with a plurality of configurable, flexible skirts along device base.
Figure 3G:
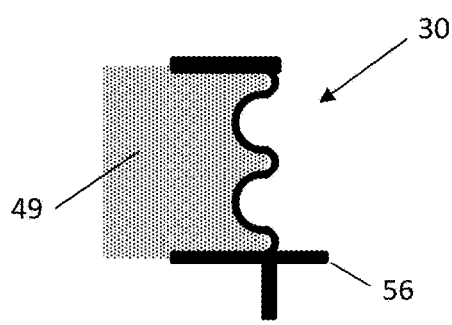
FIG. 3G is a cross-sectional view of an alternative embodiment of the device of FIG. 2A with a configurable, flexible flange along the interior fluid containment wall base.
Figure 3H:
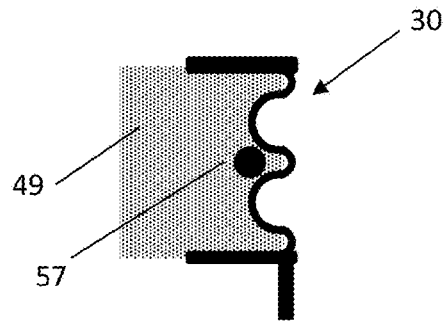
FIG. 3H is a cross-sectional view of an alternative embodiment of the device of FIG. 2A with a moldable, formable component.
Figure 3I:
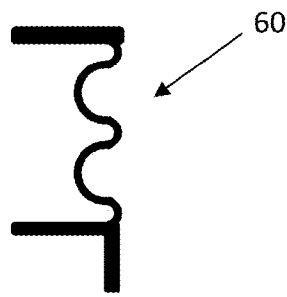
FIG. 3I is a cross-sectional view of an alternative embodiment of the device of FIG. 2A without open cell foam or other wound dressing material.
Figure 3J:
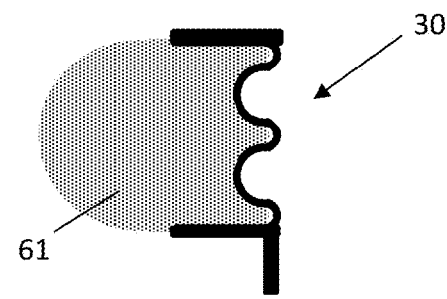
FIG. 3J is a cross-sectional view of an alternative embodiment of the device of FIG. 2A with rounded open cell foam or other wound dressing material.
Figure 3K:
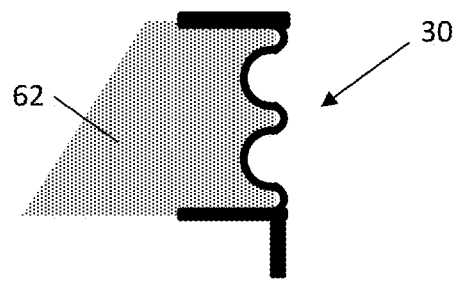
FIG. 3K is a cross-sectional view of an alternative embodiment of the device of FIG. 2A with angular open cell foam or other wound dressing material.
Figure 3L:
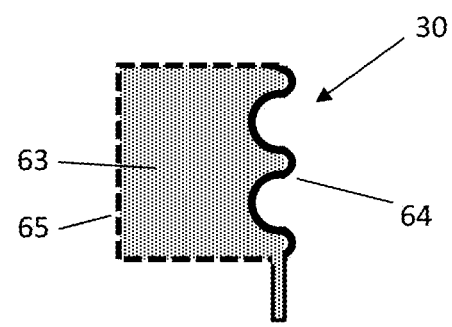
FIG. 3L is a cross-sectional view of an alternative embodiment of the device of FIG. 2A with one-piece construction.
Figure 3M:
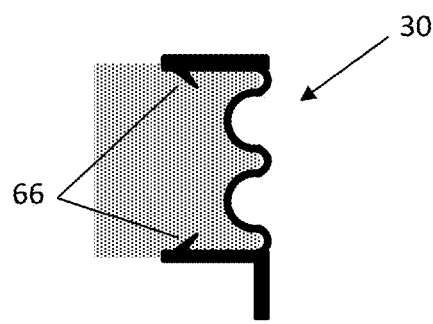
FIG. 3M is a cross-sectional view of an alternative embodiment of the device of FIG. 2A with barb(s), ridge(s), or bump(s) to retain open cell foam or other wound dressing material.
Figure 3N:
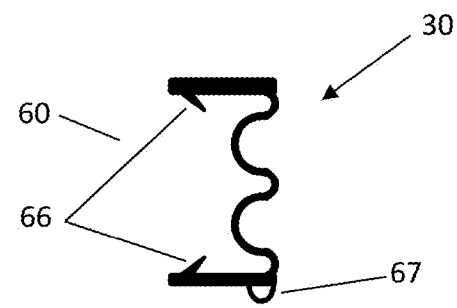
FIG. 3N is a cross-sectional view of an alternative embodiment of the device of FIG. 2A with a bulb seal along the device base.
Figure 3P:
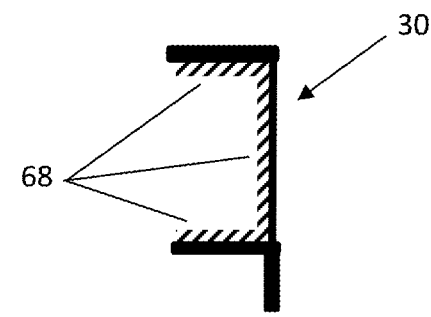
FIG. 3P is a cross-sectional view of an alternative embodiment of the device of FIG. 2A with an adhesive to retain open cell foam or other wound dressing material.

Device 30 may include any or all of the following optional features shown as alternative embodiments in FIGS. 3A, 3B, 3C, 3D, 3E, 3F, 3G, 3H, 3I, 3J, 3K, 3L, 3M, 3N and 3P. FIG. 3A shows the device 30 with a flat fluid containment wall 50. FIG. 3B shows the device 30 with a curved or convex fluid containment wall 51; however concave curves can also be contemplated. FIG. 3C shows the device 30 with ribbing 52 in the fluid containment wall. FIG. 3D shows the device 30 with bellows 53 in the fluid containment wall. FIG. 3E shows the device 30 with the skirt absent 54 from the device base 46. FIG. 3F shows the device 30 with a plurality of configurable, flexible skirts 55 along device base 46. FIG. 3G shows the device 30 with a configurable, flexible flange 56 along the interior fluid containment wall base 46. FIG. 3H shows the device 30 with a moldable, formable component 57, for example, a length of wire or bar which holds device 30 in a desired form when bent to shape. FIG. 3I shows the device 60 with open cell foam or other wound dressing material absent from the outside of the device 60. FIG. 3J shows the device 30 with a rounded strip of open cell foam or other wound dressing material 61 attached to the outside of the device 30. FIG. 3K shows the device 30 with an angular strip of open cell foam or other wound dressing material 62 attached to the outside of the device 30. FIG. 3L shows a compressible unitary construction 63 of device 30 with exterior fluid containment surface(s) 64 impermeable to liquid and air and other exterior surface(s) 64 permeable to liquid and air. FIG. 3M shows the device 30 with barb(s), ridge(s), and/or bump(s) 66 to retain open cell foam or other wound dressing material. FIG. 3N shows the device 30 with a flexible bulb seal, either solid or hollow, along the device base as a secondary means for creating a seal at the wound bed interface to contain effluent. FIG. 3P shows the device 30 with adhesive backing 68 to retain open cell foam or other wound dressing material.

Any of these various options shown as alternative embodiments in FIGS. 3A, 3B, 3C, 3D, 3E, 3F, 3G, 3H, 3I, 3J, 3K, 3L, 3M, 3N, and 3P may be used alone or in any combination on device 30. For examplary purposes only, sidewall 40 in FIGS. 3F-3N depict a pleated sidewall as shown in FIG. 3E. One of ordinary skill in the art would recognize that sidewall 40 and pleats 46 can be substituted for the sidewalls and features of the other embodiments of FIGS. 3A-3D, with no limitation.

Figure 4C:
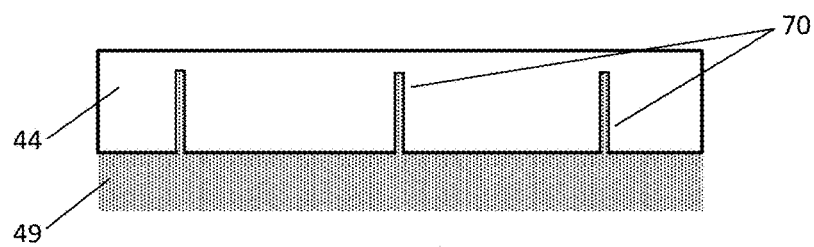
FIG. 4C is a top view of the device of FIG. 4A showing cuts or cut lines in flange on device top surface.
Figure 4B:
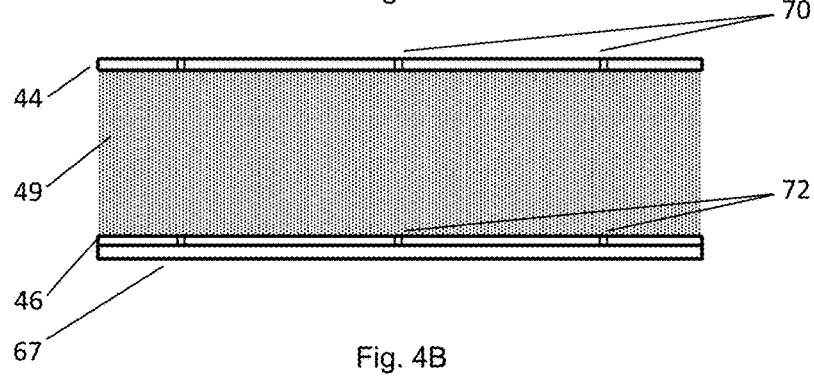
FIG. 4B is an outside view of the device of FIG. 4A showing cuts or cut lines in device flanges.
Figure 4A:
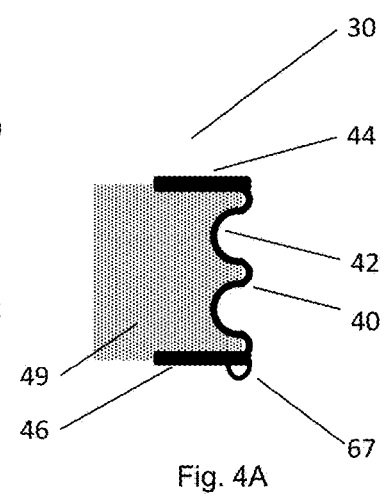
FIG. 4A is a cross-sectional view of an of an alternative embodiment of the device of FIG. 2A.
Figure 4D:
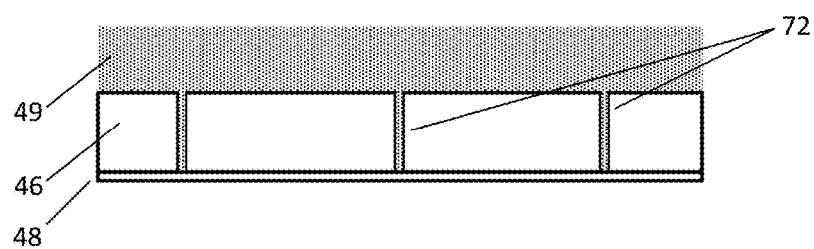
FIG. 4D is a bottom view of the device of FIG. 4A showing cuts or cut lines in flange on device base.
Figure 5C:
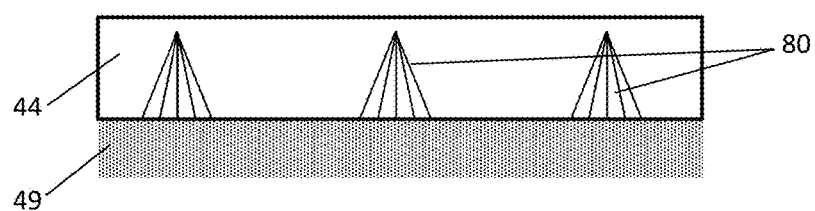
FIG. 5C is a top view of the device of FIG. 5A showing pleats or folds in flange on device top surface.
Figure 5B:
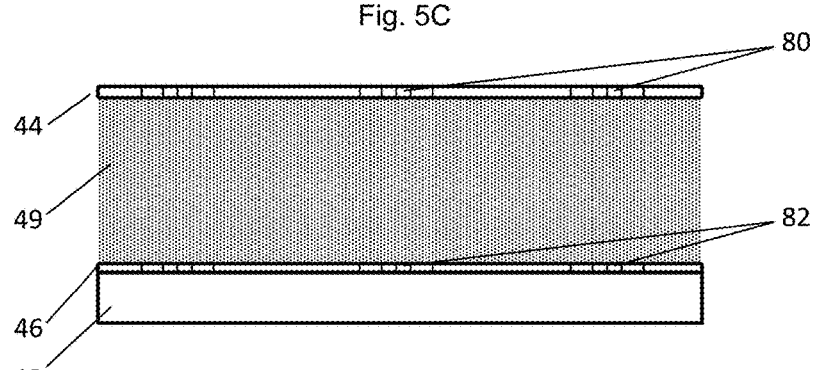
FIG. 5B is an outside view of the device of FIG. 5A showing pleats or folds in device flanges.
Figure 5A:
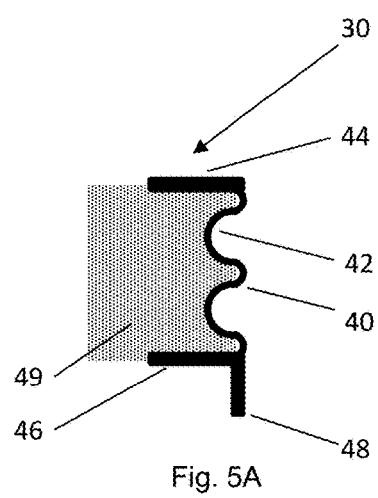
FIG. 5A is a cross-sectional view of an of an alternative embodiment of the device of FIG. 2A.
Figure 5D:
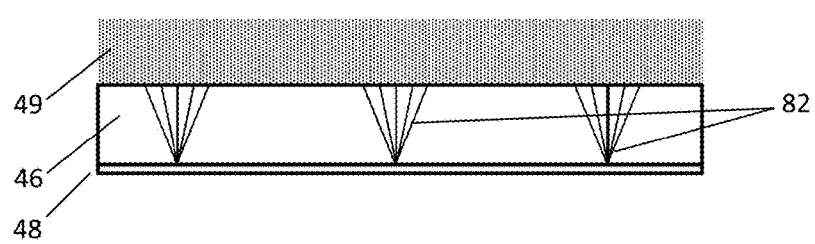
FIG. 5D is a bottom view of the device of FIG. 5A showing pleats or folds in flange on device base.
Figure 6C:
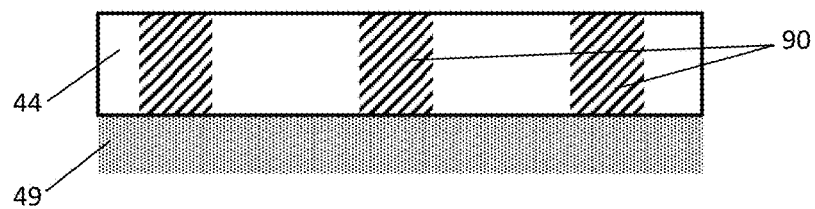
FIG. 6C is a top view of the device of FIG. 6A showing stretchable or moldable sections in flange on device top surface.
Figure 6B:
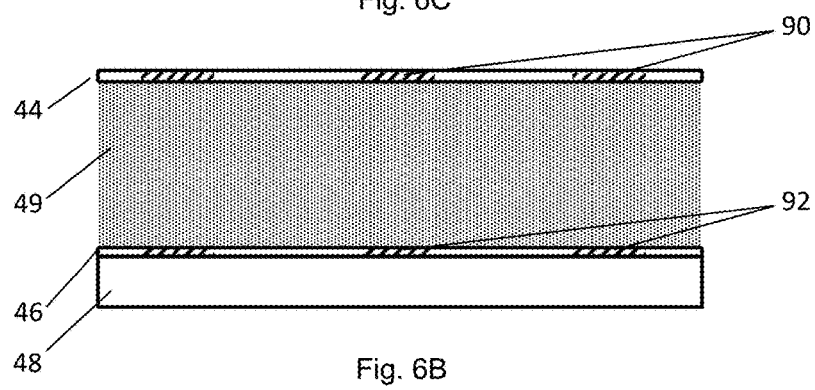
FIG. 6B is an outside view of the device of FIG. 6A showing stretchable or moldable sections in device flanges.
Figure 6A:
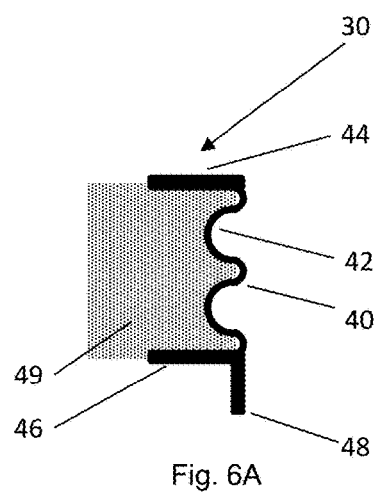
FIG. 6A is a cross-sectional view of an of an alternative embodiment of the device of FIG. 2A.
Figure 6D:
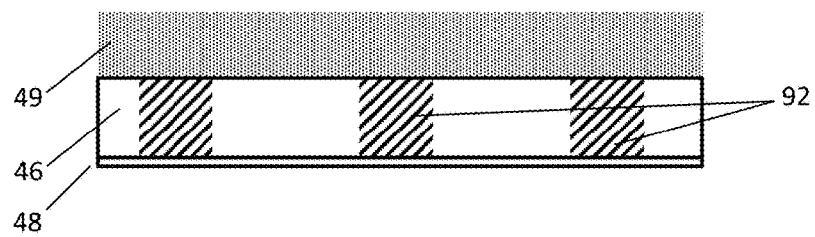
FIG. 6D is a bottom view of the device of FIG. 6A showing stretchable or moldable sections in flange on device base.

Device 30 may also include any or all of the following optional features shown as alternative embodiments in FIGS. 4A, 4B, 4C and 4D, FIGS. 5A, 5B, 5C and 5D, and FIGS. 6A, 6B, 6C and 6D. FIGS. 4B and 4C show cuts or cut lines 70 in the configurable flexible flange on the device top surface 44. FIGS. 4B and 4D show cuts or cut lines in the configurable flexible flange on the device base 46. FIGS. 5B and 5C show pleats or folds 80 in the configurable flexible flange on the device top surface 44. FIGS. 5B and 5D show pleats or folds 82 in the configurable flexible flange on the device base 46. FIGS. 6B and 6C show stretchable or moldable sections 90 in the configurable flexible flange on the device top surface 44. FIGS. 6B and 6D show stretchable or moldable sections 92 in the configurable flexible flange on the device base 46.

Any of these various options shown as alternative embodiments in FIGS. 4A, 4B, 4C and 4D, FIGS. 5A, 5B, 5C and 5D, and FIGS. 6A, 6B, 6C and 6D may be used alone or in any combination on device 30 as a mechanism for forming the device 30 into open or closed shapes to fit wounds of various shape and size.

The various embodiments of devices described herein may be made of any material suitable for the purposes described above, as will be recognized by those skilled in the art. Thus, in certain embodiments, the containment devices for the treatment of intestinal fistulas and complex wounds, or at least a portion thereof, may be made of any biocompatible materials, for example, plastics or rubber. In one particular embodiment, the fluid containment wall may be a silicone rubber. Other materials may be used, for example, a flexible thermoplastic. Preferably, the fluid containment wall is non-fluid permeable and/or non-porous. Further, as will be recognized by those skilled in the art, the devices can be sized and shaped to accommodate all different sizes and shapes of fistulas and/or wounds.

In embodiments, one or more devices according to the embodiments may be provided as a kit with instructions for use, and optionally with wound dressing material. In an embodiment, the instructions for use can include the following or similar steps for surrounding a fistula, though fewer or additional steps can be provided and the steps can be provided in other orders:

1. Disinfect device per institutional protocol. Locate bulb seal (if present) or skirt (if present) along bottom flange of device. Bulb seal or skirt is designed to be placed DOWN in the wound bed.
2. Cut hole in wound dressing centered over fistula or wound.
3. Insert device around perimeter of dressing hole until it overlaps itself or forms a butt splice. If petals formed in the flanges, cut strip so that at least one full petal overlaps another petal on the opposite end of the strip. Ensure top flange is seated on top of wound dressing and bottom flange is flush with bottom of wound dressing.
4. Prepare wound bed. Place assembled device and dressing onto wound bed so that device opening is centered over fistula or wound opening.
5. Seal entire dressing assembly with clear drape. Begin negative pressure wound therapy if prescribed. Cut drape from inner ring. If seal is lost, try stoma paste inside device base. Apply collection appliance to top flange.

In an embodiment, the instructions for use can include the following or similar steps for walling off a fistula from the rest of a wound bed area, though fewer or additional steps can be provided and the steps can be provided in other orders:

1. Disinfect device per your institutional protocol. Locate bulb seal or skirt along bottom flange of device. Bulb seal or skirt is designed to be placed DOWN in the wound bed.
2. Cut wound dressing to fit wound bed and the isolate fistula or wound opening.
3. Apply device along perimeter of dressing. Cut strip to length required. Ensure top flange is seated on top of wound dressing and bottom flange is flush with bottom of wound dressing.
4. Prepare wound bed. Place assembled device and dressing onto wound bed so that device is between fistula and wound dressing.
5. Seal entire dressing assembly with clear drape. Begin negative pressure wound therapy if prescribed. Cut drape from area over fistula. If seal is lost, try stoma paste inside device base. Apply collection appliance to top flange.

Accordingly, described herein are various embodiments of devices to contain and control the effluent and bowel contents from intestinal fistulas; these devices are adaptable to other fistulas, stomas, and other wound types. Described is, for example, a device to contain and control the effluent of intestinal fistulas, the device comprising: (a) a flexible fluid containment lineal strip, (b) fluid containment walls which collapse when pressure is applied to the wound dressing, (c) means for forming the lineal strip into open or closed shapes to fit wounds of various shape and size, (d) means for joining the lineal strip to create closed effluent containment areas, (e) means for creating a seal at the wound bed interface whereby effluent is contained, and (f) means for interfacing with a pouch appliance to capture effluent and bowel contents.

Additionally, the various embodiments have numerous advantages:

simple construction so device and dressings can be applied and changed by nonspecialized bedside or homecare nurses;

positive seals to the wound bed do not allow effluent to be drawn past the seal with NPWT or other wound care techniques which extends dressing life and establishes effective conditions for wound healing;

skirt or bulb seal which aligns device around a fistula or wound and holds device in the intended location with NPWT and other wound therapies during normal daily activity of the patient;

seal design and textured flanges mitigate the need for ostomy adhesive which reduces the frequency of wound dressing changes due to ostomy adhesive failure;

device flanges and skirt can be custom cut at bedside to best fit the device to irregular wound beds and a fistula or wound that is in close proximity to the sides of the wound bed;

devices are flexible and compresses symmetrically when part of NPWT or other wound therapies to prevent deformation or buckling over and related aggravation of the fistula or wound;

devices isolate the fistula or wound from NPWT vacuum thus protecting the bowel or wound site from negative pressures;

devices improve quality of life by allowing patients to return to their normal life and work routines during the healing process Thus, embodiments of the CONTAINMENT DEVICES FOR TREATMENT OF INTESTINAL FISTULAS AND COMPLEX WOUNDS are disclosed. The implementations described above and other implementations are within the scope of the following claims. One skilled in the art will appreciate that the present invention can be practiced with embodiments other than those disclosed, such as, for example, but not limited to, those disclosed in U.S. Pat. No. 9,078,990, entitled "DEVICES AND METHODS FOR TREATMENT OF FISTULAS AND COMPLEX WOUNDS", incorporated herein by reference in its entirety. For example, the device fluid containment wall could have other shapes; flanges could intersect the fluid containment wall at various angles; a plurality of skirts could be added to the length of the fluid containment wall; the skirts could have other cross-sectional shapes with bulbs, fins, ribbing or pleats; the device could be coated or impregnated with chemical or biological material to accelerate wound healing; etc. The disclosed embodiments are presented for purposes of illustration and not limitation, and the present invention is limited only by the claims that follow.

What is claimed is:

1. A method for using a customizable device to manage effluent or bowel contents drainage from an intestinal fistula or ostomy of a patient comprising an opening from an intestine to a skin surface of the patient; and a bed of skin surface surrounding the opening, the method comprising:
   providing the customizable device comprising:
      (i) a trimmable and flexible elongate lineal strip comprising a sidewall;
      (ii) a sealing flange extending from a first longitudinal edge of the sidewall; and
      (iii) an appliance interface flange extending from a second longitudinal edge of the sidewall;
   cutting at least one of the elongate lineal strip, the sealing flange, or the appliance interface flange, to provide a cut device of desired size that is dimensioned to border at least a portion of the opening;
   applying the cut device to the bed such that the cut device borders at least a portion of the opening, and the sealing flange forms a seal around at least a portion of the opening, thereby physically isolating the opening from the bed; and
   applying negative pressure to the sidewall to collapse the sidewall along an axis perpendicular to a length of the cut lineal strip from a first height to a second height less than the first height.

2. The method of claim 1, wherein the customizable device further comprises one or more configurable flexible skirts or bulbs depending from the first longitudinal edge, the one or more skirts or bulbs at least partially extending around or within the opening to create a seal at a bed interface between the opening and the bed.

3. The method of claim 1, wherein either or both of the sealing flange and the appliance interface flange include a plurality of independently flexible tabs.

4. The method of claim 3, wherein the one or more tabs of either or both of the sealing flange and the appliance interface flange are separated by one or more slits.

5. The method of claim 3, wherein the one or more tabs of either or both of the sealing flange and the appliance interface flange are separated by one or more pleats.

6. The method of claim 3, wherein the one or more tabs of either or both of the sealing flange and the appliance interface flange are separated by one or more sections of stretchable or moldable material.

7. The method of claim 1, further comprising coupling a wound dressing material to the cut device, wherein either or both of the sealing flange and the appliance interface flange include barbs, ridges, or bumps extending therefrom that retain the wound dressing material coupled to the cut device.

8. The method of claim 1, further comprising coupling a wound dressing material to the cut device, wherein any or all of the cut lineal strip, sealing flange, and/or appliance interface flange include an adhesive material on an outer surface thereof that retain the would dressing material to the device.

9. The method of claim 1, wherein the sidewall includes structure defining ribs or pleats to facilitate shifting between the first height and the second height.

10. The method of claim 1, further comprising a length of wire or bar coupled to the sidewall and adapted to hold the cut lineal strip in a desired form when bent to shape.

11. The method of claim 1, wherein the cut lineal strip is configured to collapse from a first height of at least 1 inch to a second height of less than 1 inch.

12. The method of claim 1, wherein the customizable device is coated or impregnated with chemical or biological material to accelerate wound healing.

13. A method for providing a customizable device to manage effluent or bowel contents drainage from an intestinal fistula or ostomy of a patient comprising an opening from an intestine to a skin surface of the patient and a bed of the skin surface surrounding the opening, the method comprising:
   providing the customizable device comprising:
      (i) a trimmable and flexible elongate lineal strip comprising a sidewall;
      (ii) a sealing flange extending from a first longitudinal edge of the sidewall; and
      (iii) an appliance interface flange extending from a second longitudinal edge of the sidewall,
   wherein at least one of the elongate lineal strip, the sealing flange, or the appliance interface flange, is configured to be cut to provide a cut device of desired size that is dimensioned to border at least a portion of the opening;
   wherein the cut device is configured to be applied to the bed such that: the cut device borders at least a portion of the opening; and the sealing flange forms a seal around at least a portion of the opening, thereby physically isolating the opening from the bed; and
   wherein the cut device is configured to have negative pressure applied to the sidewall to collapse the sidewall along an axis perpendicular to a length of the cut lineal strip from a first height to a second height less than the first height.

14. The method of claim 13, wherein the providing the customizable device comprises the providing the customizable device in a kit, wherein the kit comprises:
   the customizable device;
   a length of wound dressing coupled to the sidewall of the customizable device; and
   instructions indicating administration by cutting the elongate lineal strip to a length sufficient to at least partially surround the opening, manipulating the elongate lineal strip to a shape conforming to the opening such that the sealing flange is flush with the bed, the attached wound dressing fills the bed, and the appliance interface flange is flush with a top surface of the wound dressing opposite the sealing flange, and positioning the cut device with attached wound dressing in the opening such that the sidewall of the cut strip isolates the opening from the attached wound dressing.

15. A customizable device made according to the method of claim 13, comprising:
   the trimmable and flexible elongate lineal strip comprising the sidewall;
   (ii) the sealing flange extending from the first longitudinal edge of the sidewall; and
   (iii) the appliance interface flange extending from the second longitudinal edge of the sidewall.

16. The customizable device of claim 15, further comprising one or more configurable flexible skirts or bulbs depending from the first longitudinal edge, the one or more skirts or bulbs at least partially extending around or within the opening to create a seal at a bed interface between the opening and the bed.

17. The customizable device of claim 15, wherein either or both of the sealing flange and the appliance interface flange include a plurality of independently flexible tabs, wherein the one or more tabs of either or both of the sealing flange and the appliance interface flange are separated by one or more slits, one or more pleats, or one or more sections stretchable or moldable material.

18. The customizable device of claim 15, wherein either or both of the sealing flange and the appliance interface flange include barbs, ridges, or bumps extending therefrom, and configured to retain a wound dressing material coupled to the cut device.

19. The customizable device of claim 15, wherein the sidewall includes structure defining ribs or pleats to facilitate shifting between the first height and the second height.

20. The customizable device of claim 15, further comprising a length of wire or bar coupled to the sidewall and adapted to hold the strip in a desired form when bent to shape.

* * * * *